(12) United States Patent
Morimoto et al.

(10) Patent No.: US 7,706,886 B2
(45) Date of Patent: *Apr. 27, 2010

(54) OPHTHALMIC TREATMENT STIMULATION METHOD FOR INHIBITING DEATH OF RETINAL CELLS

(75) Inventors: Takeshi Morimoto, Toyonaka (JP); Tomomitsu Miyoshi, Ikoma (JP); Takashi Fujikado, Toyonaka (JP); Yasuo Tano, Kobe (JP); Yutaka Fukuda, Toyonaka (JP)

(73) Assignee: Nidek Co., Ltd., Gamagori-shi (JP)

( * ) Notice: Subject to any disclaimer, the term of this patent is extended or adjusted under 35 U.S.C. 154(b) by 531 days.

This patent is subject to a terminal disclaimer.

(21) Appl. No.: 11/333,242

(22) Filed: Jan. 18, 2006

(65) Prior Publication Data

US 2006/0116740 A1    Jun. 1, 2006

Related U.S. Application Data

(62) Division of application No. 10/185,003, filed on Jul. 1, 2002, now Pat. No. 7,020,527.

(30) Foreign Application Priority Data

Jan. 23, 2002   (JP)   ............................ 2002-14777

(51) Int. Cl.
*A61N 1/36* (2006.01)
(52) U.S. Cl. .......................................... 607/50; 607/53
(58) Field of Classification Search .................. 607/50, 607/53
See application file for complete search history.

(56) References Cited

U.S. PATENT DOCUMENTS 4,232,680 A    11/1980   Hudleson et al.
4,603,697 A    8/1986    Kamerling (Continued)

FOREIGN PATENT DOCUMENTS

EP    0 325 201 A2    7/1989

(Continued)

OTHER PUBLICATIONS

Miyoshi, Tomomitsu, Morimoto Takeshi, Fujikado, Takashi, Tano, Yasuo and Fukuda, Yutaka, "Inhibition of Neuronal Death of Retinal Ganglion Cell by Nerve Activation Using Electrical Stimulation," Vision Forum, 5th Annual Meeting, The Kitakyushu Science and Research Park Open Commemorative Project Assent: "Symposium of Visual Neuroscience and IT."

(Continued)

*Primary Examiner*—Kennedy J Schaetzle
(74) *Attorney, Agent, or Firm*—Oliff & Berridge, PLC

(57) ABSTRACT

An ophthalmic treatment method for inhibiting death of retinal constitutive cells of an eye by stimulating the cells includes a first step of placing a positive electrode and a negative electrode in such positions outside the eye that the electrodes provide electrical stimulation to the cells, at least one of the electrodes being placed on one of a cornea and sclera of the eye; and a second step of generating an electrical stimulation pulse having an electric current set at 20 μA or more but not exceeding 300 μA from each placed electrode.

5 Claims, 4 Drawing Sheets

U.S. PATENT DOCUMENTS

| | | | |
|---|---|---|---|
| 4,955,378 A * | 9/1990 | Grasso .................. 607/53 |
| 5,147,284 A * | 9/1992 | Fedorov et al. .............. 600/9 |
| 5,522,864 A | 6/1996 | Wallace et al. |
| 5,895,415 A * | 4/1999 | Chow et al. ................ 607/54 |
| 6,101,411 A | 8/2000 | Newsome |
| 7,003,355 B1 * | 2/2006 | Suaning et al. ............. 607/54 |
| 7,020,527 B2 * | 3/2006 | Morimoto et al. ........... 607/50 |
| 7,142,909 B2 * | 11/2006 | Greenberg et al. ........... 607/2 |
| 2004/0106965 A1 * | 6/2004 | Chow ...................... 607/54 |

FOREIGN PATENT DOCUMENTS

| | | |
|---|---|---|
| JP | A 8-154897 | 6/1996 |
| JP | A 9-266954 | 10/1997 |
| JP | A 2000-24122 | 1/2000 |

OTHER PUBLICATIONS

Morimoto, Takeshi, Miyoshi, Tomomitsu, Fujikado, Takashi, Tano, Yasuo and Fukuda, Yutaka, "Electrical stimulation enhances the survival of axotomized retinal ganglion cells in vivo," NEUROREPORT, vol. 13, No. 2, Feb. 11, 2002, pp. 227-230 and Erratum.

Yokoyama, Akiko, Oshitari, Toshiyuki, Negishi, Hisanari, Dezawa, Mari, Mizota, Atushi and Adachi-Usami, Emiko, "Protection of Retinal Ganglion Cells from Ischemia-Reperfusion Injury by Electrically Applied Hsp27," Investigative Ophthalmology & Visual Science, Dec. 2001, vol. 42, No. 13, pp. 3283-3286.

* cited by examiner

FIG.5

Table 1

| | WAVEFORM | CURRENT (μA) | DURATION (μs) | FREQUENCY (Hz) | TREATMENT TIME (h) | DAMAGE | SURVIVAL RATE (%) | COMPREHENSIVE EVALUATION |
|---|---|---|---|---|---|---|---|---|
| EXPERIMENT 1 | MONO | 20 | 50 | 20 | 2 | NONE | 64 | ○ |
| EXPERIMENT 2 | MONO | 30 | 50 | 20 | 2 | NONE | 76 | ○ |
| EXPERIMENT 3 | MONO | 50 | 50 | 20 | 2 | NONE | 83 | ○ |
| EXPERIMENT 4 | MONO | 70 | 50 | 20 | 2 | NONE | 75 | ○ |
| COMPARATIVE EXPERIMENT 1 | MONO | \multicolumn{4}{NO ELECTRODE BEING SET} | NONE | 54 | × |
| COMPARATIVE EXPERIMENT 2 | MONO | 0 | 0 | 0 | 0 | NONE | 53 | × |

(MONO = MONOPHASIC WAVE)

FIG.6

Table 2

| | WAVEFORM | CURRENT (μA) | DURATION (ms) | FREQUENCY (Hz) | TREATMENT TIME (h) | DAMAGE | SURVIVAL RATE (%) | COMPREHENSIVE EVALUATION |
|---|---|---|---|---|---|---|---|---|
| EXPERIMENT 5 | MONO | 100 | 1 | 5 | 1 | NONE | 71.8 | ○ |
| COMPARATIVE EXPERIMENT 3 | MONO | \multicolumn{5}{c}{NO ELECTRODE BEING SET} | NONE | 54 | × |
| COMPARATIVE EXPERIMENT 4 | MONO | 100 | 2 | 5 | 1 | SOME | NO EVALUATION | × |
| COMPARATIVE EXPERIMENT 5 | MONO | 100 | 3 | 5 | 1 | SOME | NO EVALUATION | × |

(MONO = MONOPHASIC WAVE)

ically viewed from a patient's eye. Numeral 2 is an electrical stimulation pulse generator which generates electrical stimulation pulses from the electrode 1. This pulse generator 2 is arranged such that various conditions of the electrical stimulation pulses (e.g., pulse waveform, electric current intensity, wavelength, duration of electric current, and frequency) can be set changeably by operation of a control part 2a. The electrode 1 is connected to the pulse generator 2 through a connection cable 3.

OPHTHALMIC TREATMENT STIMULATION METHOD FOR INHIBITING DEATH OF RETINAL CELLS

This is a Divisional application of U.S. patent application Ser. No. 10/185,003 filed Jul. 1, 2002, now issued as U.S. Pat. No. 7,020,527. The entire disclosure of the prior application is hereby incorporated by reference herein in its entirety.

BACKGROUND OF THE INVENTION

1. Field of the Invention

The present invention relates to an ophthalmic treatment apparatus capable of protecting cells constituting a retina.

2. Description of Related Art

Recently, there have been known ophthalmic diseases such as glaucoma, ischemic retinal degeneration, and optic nerve injury. In these diseases, a retinal ganglion cell which is one of cells of the kind constituting a retina (hereinafter, retinal constitutive cells) degenerates and comes to death, which causes gradual loss of patient's good eyesight. This may lead to blindness when the diseases continue to progress. As yet, there are no effective treatments for such diseases. A vitamin preparation and a blood-flow improving medication are usually used as therapeutic agents (medicines) for the diseases; however, reliable therapeutic effect could not be produced actually. In basic experiments using animals, on the other hand, there has been known that the use of a neurotrophic factor such as BDNF (brain-derived neurotrophic factor) as a therapeutic agent could delay the death of the retinal constitutive cells or improve the function of these cells.

However, it is desirable to keep administration of the above mentioned therapeutic agents to the human body to a minimum for preventing side effects. To allow the therapeutic agents such as BDNF and others to efficiently reach the retinal constitutive cells, the therapeutic agents need to be administered by injection to vitreous body. This administration by the injection to vitreous body allows the therapeutic agents to efficiently reach the retinal constitutive cells, such as retinal ganglion cells; nevertheless, the injection to eyeball would give very uncomfortable feeling to the patient.

SUMMARY OF THE INVENTION

The present invention has been made in view of the above circumstances and has an object to overcome the above problems and to provide an ophthalmic treatment apparatus with a simple structure capable of inhibiting death of retinal constitutive cells.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an ophthalmic treatment apparatus including: an electrode which is set on a place to apply electrical stimulation to cells constituting a retina; and an electrical stimulation pulse generator which is connected to the electrode, for generating, from the electrode, a predetermined electrical stimulation pulse whose electric current is set at 20 µA or more but not exceeding 300 µA.

According to another aspect of the present invention, an ophthalmic treatment apparatus including: an electrode having a shape like a contact lens, which is placed on a cornea; and an electrical stimulation pulse generator which is connected to the electrode, for generating a predetermined electrical stimulation from the electrode.

Furthermore, according to another aspect of the present invention, an ophthalmic treatment apparatus including: an electrode having a positive pole and a negative pole, which is placed so that the negative pole is positioned on a retinal side with respect to the positive pole; and an electrical stimulation pulse generator which is connected to the electrode, for generating a predetermined electrical stimulation from the electrode.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 5 is a table 1 showing results of experiments 1-4 and comparative experiments 1 and 2; and FIG. 6 is a table 2 showing results of an experiment 5 and comparative experiments 3-5.

DETAILED DESCRIPTION OF THE PREFERRED EMBODIMENTS

Figure 1:
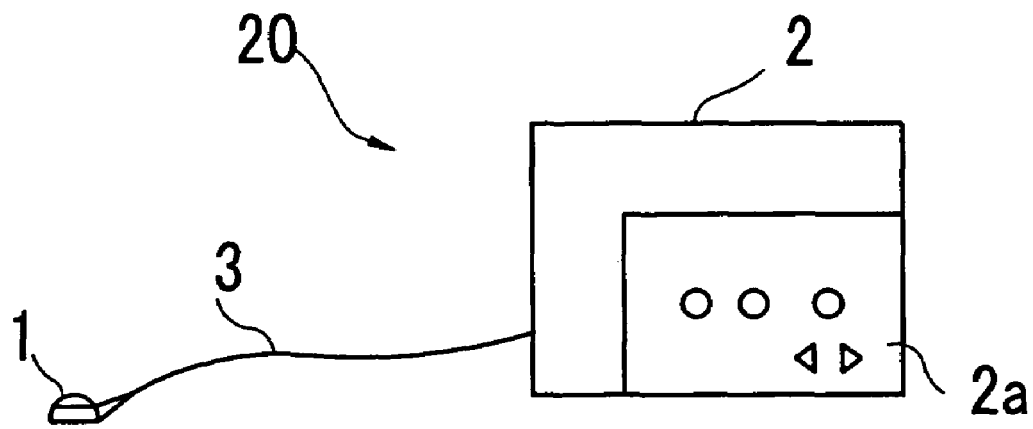
FIG. 1 is a schematic perspective view of an ophthalmic treatment apparatus in an embodiment according to the present invention.

A detailed description of preferred embodiments of an ophthalmic treatment apparatus embodying the present invention will now be given referring to the accompanying drawings. FIG. 1 is a schematic perspective view of an ophthalmic treatment apparatus 20. This apparatus 20 is structured to stimulate (fire) retinal constitutive cells, e.g., retinal ganglion cells, retinal bipolar cells, retinal horizontal cells, photoreceptor cells, and retinal pigment epithelial cells, by passage of a small amount of electric current through an electrode set on a patient's eye, thereby inhibiting death of the cells.

Numeral 1 is an electrode which is placed over a cornea of the patient's eye. Numeral 2 is an electrical stimulation pulse generator which generates electrical stimulation pulses from the electrode 1. This pulse generator 2 is arranged such that various conditions of the electrical stimulation pulses (e.g., pulse waveform, electric current intensity, wavelength, duration of electric current, and frequency) can be set changeably by operation of a control part 2a. The electrode 1 is connected to the pulse generator 2 through a connection cable 3.

Figure 2:
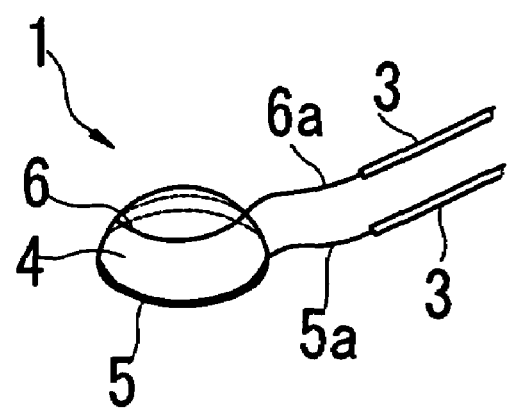
FIG. 2 is a schematic structural view of an electrode.

FIG. 2 is a schematic structural view of the electrode 1. The electrode 1 is constructed of a body 4 which is placed over the cornea and a pair of electrode parts 5 and 6. The body 4 has a shape like a contact lens whose inner wall surface conforms (fits) in shape to the corneal surface. The body 4 may be made of any insulating materials and does not necessarily require being transparent like a contact lens.

The electrode part 5 is a negative electrode (negative pole) which is provided annularly at a peripheral edge of the body 4. The electrode part 6 is a positive electrode (positive pole) which is provided at an intermediate position between the vertex and the peripheral edge of the body 4 to appear circularly on the inner wall surface which will contact the corneal surface during use. It is to be noted that each formation (arrangement) position of the positive and negative electrodes is not limited to above and may be determined to arrange the negative pole on the retinal side in order to efficiently stimulate (fire) the cells.

Those electrode parts 5 and 6 may be made of usually used electrode materials such as platinum, gold, and silver. Electric wires 5a and 6a are connected to the electrode parts 5 and 6 respectively. The other ends of the wires 5a and 6a are connected to the pulse generator 2 through the connection cable 3 which is an insulative tube.

The operation of the ophthalmic apparatus having the above structure will be explained below.

Figure 3:
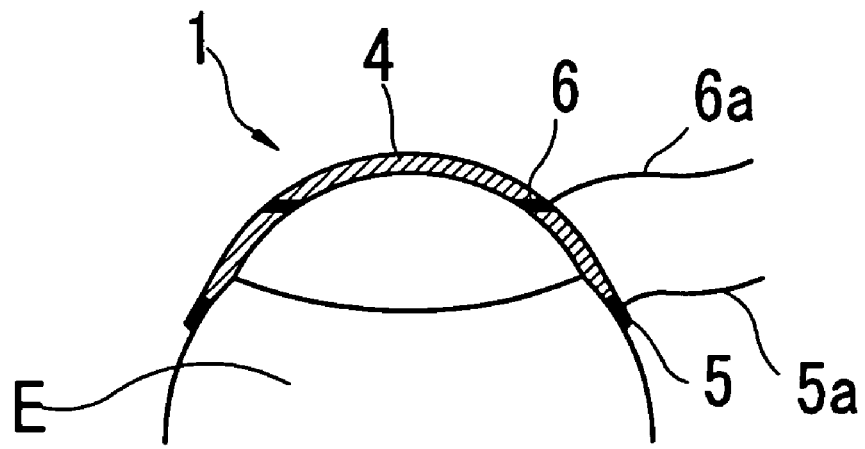
FIG. 3 is an explanatory view showing a state where the electrode is placed over a patient's eye.

At first, a patient is laid on his back on a surgical bed. An operator places the electrode 1 over a patient's eye E as shown in FIG. 3 and sets electrical stimulation pulse conditions with the control part 2a of the pulse generator 2 to generate electrical stimulation pulses from the electrode 1, thereby stimulating (firing) retinal ganglion cells of the eye E.

The preferable conditions of the electrical stimulation pulses are as described below.

The electric current intensity is preferably 20 μA or more but not exceeding 300 μA. This is because the current of less than 20 μA is incapable of stimulating (firing) the retinal constitutive cells such as retinal ganglion cells. Thus, no treatment effect can be provided. On the other hand, the current of more than 300 μA may cause retinal detachment and vitreous hemorrhage due to a large amount of electric current, which would damage a living body. Furthermore, the current is more preferably set in a range from 40 μA to 200 μA, particularly from 50 μA to 120 μA.

The duration of electric current is preferably 50 μs or more but not exceeding 10 ms. This is because the duration of less than 50 μs cannot provide a treatment effect and the duration of more than 10 ms may damage the living body. Furthermore, the duration is more preferably set in a range from 100 μs to 5 ms, particularly from 1 ms to 3 ms.

The frequency is preferably 1 Hz or more but not exceeding 100 Hz. This is because the frequency of less than 1 Hz can produce no treatment effect and the frequency of more than 100 Hz may damage the living body. Furthermore, the frequency is more preferably set in a range from 3 Hz to 40 Hz, particularly 5 Hz to 30 Hz.

The treatment time for which the treatment is performed by passing the electrical stimulation pulses (i.e. the application time of the electrical stimulation pulses) is preferably 10 min. or more but not exceeding 5 hours. This is because the treatment time of less than 10 min. cannot provide a desired effect and the treatment time of more than 5 hours may damage the living body. Furthermore, the treatment time is more preferably set in a range from 20 min. to 3 hours, particularly from 30 min. to 1 hour.

The pulse waveform may be chosen between a monophasic wave and a biphasic wave; preferably the biphasic wave. In the case of the monophasic wave, a positive pole and a negative pole do not alternate, which causes a similar phenomenon to electrophoretic migration on the cornea. In that state, protein in tear (lacrimal fluid) is likely to be attracted to the positive electrode and accrete thereto. If the protein accretes to the positive electrode, increasing a resistance value, the electrode may liberate heat. This heat may cause degeneration of the cornea. When the monophasic wave is chosen, therefore, it is necessary to set a low upper limit on each condition of the electrical stimulation pulse as compared with the case where the biphasic wave is used.

After the electrode 1 is placed over the patient's eye E as above, the electrical stimulation pulses are applied to the retinal constitutive cells, thereby stimulating (firing) the cells, to inhibit death of the cells.

In the present embodiment, the electrode 1 having a contact lens shape is placed over the cornea for execution of electrical stimulation, but it is not limited thereto. Any shape or type of electrode may be used if only it can perform the application of electrical stimulation pulses to the retinal constitutive cells. For instance, not only the electrode of the contact lens shape but also an electrode of a sheet shape, a rod shape, or other shapes may be used.

The placing position of the electrode 1 is not limited to on the cornea. The electrode may be placed on any position if only the electrode can apply electrical stimulation pulses to the cells. For example, the electrode may be placed on the circumference of the orbit of the eye. An alternative is to place the positive pole on the cornea and the negative pole on a different region (e.g., the orbit, the ear, etc.). Furthermore, the electrode may be set on the sclera side to perform transchoroidal stimulation.

Next, animal experiments are shown as concrete examples of death inhibition effects on the cells by applying electrical stimulation pulses to the retinal ganglion cells.

At first, basic experiments were performed to determine whether the application of electrical stimulation pulses to the retinal constitutive cells had the effect of inhibiting cell death.

<Experiment 1>

Figure 4:
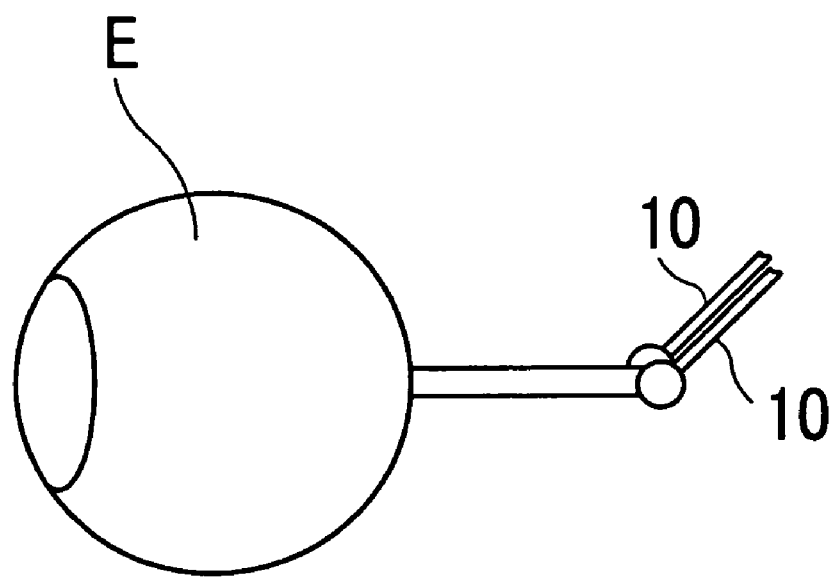
FIG. 4 is a schematic view showing a state where an electrode is attached to an optic nerve.

Experimental animals were rats (Wister rat, Male, 12 weeks old). A fluorescent dye (fluorogold) was injected into bilateral superior colliculi to retrogradely label retinal ganglion cells. Then, an optic nerve was cut (transected) and immediately silver-ball bipolar electrodes 10 were attached to the end of optic nerve stump (see FIG. 4) to apply thereto electrical stimulation pulses. The conditions of the electrical stimulation pulses were set as follows: waveform: monophasic wave, current: 20 μA, duration: 50 μs, frequency: 20 Hz, and treatment time: 2 hours.

After one week, a fluorescent microscope (Axioskop manufactured by Carl Zeiss) with a U.V. filter was used to count the number of retrogradely labeled cells (retinal ganglion cells) in 12 areas on a retina. Then, the densities of the labeled cells per 1 mm$^2$ at 12 areas were averaged to provide an average density. On the other hand, an average density of cells in a normal animal (rats) to which the experiment was not performed (no electrical stimulation is applied) was also calculated for comparison to find the survival rate of the cells applied with the electrical stimulation pulses in the experiment 1. The result is shown in Table 1 (FIG. 5).

<Experiment 2>

In the electrical stimulation pulse conditions, the electric current was set at 30 μA and others were the same as in the experiment 1. Under these conditions, electrical stimulation pulses were applied to a cut optic nerve of rats. After one week, as in the experiment 1, the number of retrogradely labeled cells was counted in 12 areas on a retina. Then, an average density of the cells was calculated to obtain a survival rate. This result is shown in Table 1 (FIG. 5).

<Experiment 3>

In the electrical stimulation pulse conditions, the electric current was set at 50 μA and others were the same as in the experiment 1. Under these conditions, electrical stimulation pulses were applied to a cut optic nerve of rats. After one week, as in the experiment 1, the number of retrogradely labeled cells was counted in 12 areas on a retina. Then, an average density was calculated to obtain a survival rate. This result is shown in Table 1 (FIG. 5).

<Experiment 4>

In the electrical stimulation pulse conditions, the electric current was set at 70 μA and others were the same as in the experiment 1. Under these conditions, electrical stimulation pulses were applied to a cut optic nerve of rats. After one week, as in the experiment 1, the number of retrogradely labeled cells was counted in 12 areas on a retina. Then, an average density was calculated to obtain a survival rate. This result is shown in Table 1 (FIG. 5).

<Comparative Experiment 1>

Rats of the same kind as in the experiment 1 were used. Retinal ganglion cells were retrogradely labeled and then an optic nerve was cut, but no electrical stimulation pulse was applied thereto. After one week, the number of retrogradely labeled cells was counted in 12 areas on a retina to calculate an average density of the cells to find a survival rate. This result is shown in Table 1 (FIG. 5).

<Comparative Experiment 2>

Rats of the same kind as in the experiment 1 were used. Retinal ganglion cells were retrogradely labeled and then an optic nerve was cut. Immediately, the silver ball bipolar electrodes 10 were attached to optic nerve stump, but no electrical stimulation pulse was applied thereto. After one week, as in the experiment 1, the number of retrogradely labeled cells was counted to calculate an average density of the cells to find a survival rate. This result is shown in Table 1 (FIG. 5).

As shown in Table 1 (FIG. 5), the survival rate (cell density) of the retinal ganglion cells could be greatly increased in the cases where the electrical stimulation pulses were applied as compared with the cases where the electrical stimulation pulses were not applied.

Based on the above experimental results, experiments using the electrode of a contact lens shape were carried out.

<Experiment 5>

Rats of the same kind as in the experiment 1 were used. The treatment apparatus 20 and the electrode 1 having a shape conforming to the corneal shape of the rat were used. The electrode 1 was provided with a suction hole to prevent the electrode 1 from becoming displaced (misaligned) during treatment.

A fluorescent dye (fluorogold) was injected into bilateral superior colliculi to retrogradely label retinal ganglion cells. Then, an optic nerve was cut and immediately the electrode 1 was placed over an eyeball of the rat. Air was sucked through the suction hole to cause the electrode 1 to be adsorbed to the eyeball. In this state, electrical stimulation pulses were applied. The electrical stimulation pulse conditions were as follows: waveform: monophasic wave, current: 100 μA, duration: 1 ms, frequency: 5 Hz, and treatment time: 1 hour.

After one week, a fluorescent microscope (Axioskop manufactured by Carl Zeiss) with a U.V. filter was used to count the number of retrogradely labeled cells (retinal ganglion cells), in 12 areas on a retina. Then, the densities of the labeled cells per 1 mm$^2$ at 12 areas were averaged to provide an average density. An average density of cells in a normal animal (rats) to which the experiment was not performed (no electrical stimulation is applied) was also calculated for comparison to find a survival rate of the cells applied with the electrical stimulation pulses in the experiment 5. This result is shown in Table 2 (FIG. 6).

<Comparative Experiment 3>

Rats of the same kind as in the experiment 5 were used. Retinal ganglion cells were retrogradely labeled and then an optic nerve was cut, but any electrical stimulation pulses were not applied thereto. After one week, the number of retrogradely labeled cells was counted in 12 areas on a retina to calculate an average density thereof to find a survival rate. This result is shown in Table 2 (FIG. 6).

<Comparative Experiment 4>

In the electrical stimulation pulse conditions, the duration was set at 2 ms and others were the same as in the experiment 5. Under these conditions, electrical stimulation pulses were applied. As a result of this comparative experiment, there was found corneal degeneration due to heating by the electrode. The result is shown in Table 2 (FIG. 6).

<Comparative Experiment 5>

In the electrical stimulation pulse conditions, the duration was set at 3 ms and others were the same as in the experiment 5. Under these conditions, electrical stimulation pulses were applied. As a result of this comparative experiment, there was found corneal degeneration due to heating by the electrode. The result is shown in Table 2 (FIG. 6).

As shown in Table 2 (FIG. 6), the case where the electrical stimulation pulses were applied (Experiment 5) could remarkably inhibit death of the retinal ganglion cells as compared with the case where the electrical stimulation pulses were not applied (Comparative experiment 3). There is no large difference in structure between a rat eyeball and a human eyeball. Thus, the same effects as in the above experiments can be exerted on the human.

From the above experimental results (Experiments 1 to 5 and Comparative experiments 1 to 5), it is shown that the electric current, the duration of electric current, and others in the case where the electrode of a contact lens shape is placed on the cornea need to be set larger than those in the case where the electrode is brought into direct contact with the optic nerve in order to produce the same or similar effects as in the latter case. If the duration is set too longer as shown from the results of the comparative experiments 4 and 5, the electrode would be overheated. Thus, the electric current needs to be set lower when a long duration is desired.

The result of the experiment 5 shows that a survival rate of 71.8% could be obtained for the electric current of 100 μA. Even if the electric current is set smaller than 100 μA, therefore, the effect of inhibiting death of the cells could be obtained.

Considering the above, when the electrode is placed and used on the cornea, the survival rate is estimated at about 60% under the electrical stimulation pulse conditions; monophasic wave, current: 50 μA, duration: 1 ms, frequency: 5 Hz, and treatment time: 1 hour. The survival rate is estimated at about 70% under the electrical stimulation pulse conditions; monophasic wave, current: 50 μA, duration: 2 ms, frequency: 5 Hz, and treatment time: 1 hour. Furthermore, the survival rate is estimated at about 75% under the electrical stimulation pulse conditions; monophasic wave, current: 50 μA, duration: 3 ms, frequency: 5 Hz, and treatment time: 1 hour.

If the electric current is smaller than 50 μA, it seems slightly low to apply electrical stimulation pulses to a retina from above a cornea. In this case, the duration of electric current is set longer to exert the death inhibition effect on the cells. For example, if the electric current is about 20 μA, the survival rate is estimated at about 60% under the electrical stimulation pulse conditions; duration: 3 ms, frequency: 5 Hz, and treatment time: 1 hour.

In the case where the biphasic wave is used, the electrode can be prevented from overheating. The electric current may be set larger than that in the case of the monophasic wave. For example, it is predicted that the electrical stimulation pulse conditions; biphasic wave, current: 120 μA, duration: 1 ms, frequency: 5 Hz, and treatment time: 1 hour can ensure a survival rate of about 80% without damage to a living body. The biphasic wave can suppress damage to a living body as compared with the monophasic wave. It is thus estimated that the duration can be set at about 2 ms with the electric current set in a range from about 100 μA to about 120 μA.

In the above embodiment, the ophthalmic treatment apparatus is used independently to inhibit the death of the retinal ganglion cells. Other treatment means may be used in combination with the above apparatus. In this case, multiplier effects can be expected. These other treatment means include therapeutic agents for glaucoma, such as parasympathomimetic agents, sympathomimetic agents, and others. Administration of those therapeutic agents, if the ophthalmic treatment apparatus according to the present invention is used at the same time, can be reduced in dosage or frequency as compared with in the conventional case.

The above embodiment shows that the ophthalmic treatment apparatus can inhibit the death of the retinal ganglion cells. In addition thereto, it can be expected to inhibit death of the retinal constitutive cells, for example, retinal bipolar cells, retinal horizontal cells, photoreceptor cells, and retinal pigment epithelial cells.

As explained above, the ophthalmic treatment apparatus according to the present invention can achieve the purpose of inhibiting death of the retinal constitutive cells.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic treatment method for inhibiting death of retinal cells of an eye by stimulating the retinal cells, the method comprising:

a first step of placing a positive electrode and a negative electrode separately from each other in such positions outside the eye that the electrodes provide electrical stimulation to the retinal cells, the positive electrode being placed near a corneal vertex and the negative electrode being placed near a peripheral portion of a cornea or on a sclera of the eye; and a second step of transmitting an electrical stimulation pulse having an electric current set at such a level as to stimulate the retinal cells and not to damage a living body from an electrical stimulation pulse generator to each electrode through a cable to emit the electrical stimulation pulse from each electrode.

2. The ophthalmic treatment method according to claim 1, wherein the second step includes emitting the electrical stimulation pulse for a duration of the electric current being set at such a level as to stimulate the retinal cells and not to damage the living body from each electrode.

3. The ophthalmic treatment method according to claim 1, wherein the second step includes emitting the electrical stimulation pulse which frequency is set at such a level as to stimulate the retinal cells and not to damage the living body from each electrode.

4. The ophthalmic treatment method according to claim 1, wherein the second step includes emitting the electrical stimulation pulse for an application time being set at such a level as to stimulate the retinal cells and not to damage the living body from each electrode.

5. The ophthalmic treatment method according to claim 1, wherein the second step includes emitting the electrical stimulation pulse having a biphasic pulse waveform from each electrode.

* * * * *